(12) United States Patent
Hu

(10) Patent No.: US 12,343,182 B2
(45) Date of Patent: Jul. 1, 2025

(54) PRECISE TREATMENT POSITIONING ADAPTER FOR A TRANSCRANIAL MAGNETIC STIMULATOR

(71) Applicant: FUTON MEDICAL TECHNOOGY PTY LTD, NSW (AU)

(72) Inventor: Die Hu, NSW (AU)

( * ) Notice: Subject to any disclaimer, the term of this patent is extended or adjusted under 35 U.S.C. 154(b) by 86 days.

(21) Appl. No.: 18/135,757

(22) Filed: Apr. 18, 2023

(65) Prior Publication Data
US 2023/0397893 A1    Dec. 14, 2023

(30) Foreign Application Priority Data
Jun. 13, 2022  (CN) .......................... 202210662440.8

(51) Int. Cl.
*A61B 6/04* (2006.01)
*A61N 2/00* (2006.01)

(52) U.S. Cl.
CPC ................. *A61B 6/04* (2013.01); *A61N 2/006* (2013.01)

(58) Field of Classification Search
CPC ............. A61B 6/04; A61N 2/006; A61N 2/00
See application file for complete search history.

(56) References Cited

PUBLICATIONS

Song et al (CN 108042918) machine translation (Year: 2018).*
Ke et al (CN 112843478) machine translation (Year: 2021).*
Zhao et al (CN 113967146) machine translation (Year: 2022).*
Wu et al (CN 113559417) machine translation (Year: 2021).*

* cited by examiner

*Primary Examiner* — Alexei Bykhovski

(57) ABSTRACT

A precise treatment positioning adapter for a transcranial magnetic stimulator is disclosed. It comprises a head sleeve base body and at least one positioning and fixing structure of treatment head; the positioning and fixing structure of the treatment head is as follows: a vacancy position of the treatment head matching shape of the treatment head is arranged at a predetermined treatment position of the head cover base body; a clamping and fixing structure of the treatment head is arranged at the edge of the vacancy position of the treatment head on the outer surface of the head sleeve base body, so that the treatment head is stably clamped. The precise treatment positioning adapter for a transcranial magnetic stimulator can accurately and conveniently locate the treatment head of a large transcranial magnetic stimulator to the target that patients need to treat.

12 Claims, 5 Drawing Sheets

PRECISE TREATMENT POSITIONING ADAPTER FOR A TRANSCRANIAL MAGNETIC STIMULATOR

BACKGROUND OF THE INVENTION

This application claims priority to CN Patent Application No. 102016207365.6, which was filed on 29 Apr. 2016, the entire contents of which are expressly incorporated herein by reference.

The present disclosure relates to a medical device, and more specifically to a transcranial magnetic stimulation device.

Transcranial magnetic stimulation (TMS) is a non-invasive and few side effects neuromodulation technology, which plays a huge role in the field of cognitive neuroscience and clinical neural function regulation. TMS can use the time-varying magnetic field generated by pulse current to generate an induced electric field in brain tissue, thereby regulating neuronal excitability, stimulating specific brain function cortex, and playing a role in the treatment of various brain diseases.

After decades of development and application, transcranial magnetic stimulator has achieved good curative effect in many fields of neuromodulation, and supported by a large number of literatures. And in the process of clinical use, it has also been widely recognized by doctors in related departments.

Transcranial magnetic stimulators are divided into traditional transcranial magnetic stimulators and portable transcranial magnetic stimulators appeared in recent years. Hospitals and other institutions are generally equipped with a certain number of traditional transcranial magnetic stimulators. Due to volume, weight and other reasons of the equipment, the traditional transcranial magnetic stimulator cannot be moved conveniently, the operation of which is relatively cumbersome, and the requirements of which are high, but because of the power and other issues of the traditional transcranial magnetic stimulator, its treatment intensity and therapeutic effect can not be replaced by non-portable transcranial magnetic stimulator.

However, there are still some difficulties in practical clinical application, so that the therapeutic effect of the transcranial magnetic stimulator cannot be fully exerted, thereby benefiting more patients. The main problem is that in the process of using the transcranial magnetic stimulator, there will still be high requirements for the operator, especially for the precise positioning of the treatment target. Operators including primary medical units have all undergone certain training and can find the corresponding treatment position, but in order to achieve a good curative effect (such as the experimental results reported in many top journals at home and abroad), it is necessary to repeat the precise therapeutic targets in the experimental, which precisely requires the operator to have a strong ability to operate, otherwise the actual results will often be very different. In practice, there are also some good methods to solve this problem, such as advanced treatment navigation instruments, which can make treatment plans in advance through the analysis of the patient's MRI data by the machine, so that the treatment head of the transcranial magnetic stimulator can be quickly, accurately and conveniently placed on the corresponding treatment target, and the operator does not require too much skill. However, the price of these advanced navigation instruments, whether imported or domestic, is often as high as two or three hundred thousand, which makes many hospitals in need unable to buy them, so the penetration rate is very, very low.

In addition to the above-mentioned problem of precise positioning capability, there is also a very prominent contradiction that an experienced and competent operator often takes about an hour to operate the machine for positioning when treating a patient (if the patient accidentally moves the head during treatment, repositioning is also required). As a result, a doctor cannot treat many patients in one day even if he has a good operating ability. This further expands the actual gap and contradiction between supply and demand sides, so that the actual treatment needs of a large number of patients cannot be effectively met.

In summary, in order to better exert the therapeutic effect of transcranial magnetic stimulator, so that more patients can obtain good curative effect and improve the quality of life, in the market, it urgently needs a cheap, high-quality, simple and effective precise positioning device to solve the problem.

BRIEF SUMMARY OF THE INVENTION

The technical problem to be solved by the present disclosure is to arrange a unique and practical precise treatment positioning adapter for a transcranial magnetic stimulator, which can accurately and conveniently locate the treatment head of a large transcranial magnetic stimulator to the target that patients need to treat, which is simple, convenient, accurate and effective, thus greatly reducing the operation time of doctors and improving the curative effect, so that more patients can benefit from it.

In order to solve this technical problem, the technical scheme adopted by the present disclosure is as follows:

a precise treatment positioning adapter for a transcranial magnetic stimulator, comprising:

a head sleeve base body and at least one positioning and fixing structure of treatment head;

the positioning and fixing structure of the treatment head is as follows: a vacancy position of the treatment head matching shape of the treatment head is arranged at a predetermined treatment position of the head cover base body; a clamping and fixing structure of the treatment head is arranged at the edge of the vacancy position of the treatment head on the outer surface of the head sleeve base body, so that the treatment head is stably clamped, and the treatment surface of the treatment head pass through the vacancy position of the treatment head and then fit to the head of the patient.

Further, the clamping and fixing structure of the treatment head comprises at least two handle uprights, and the handle of the treatment head is matched and clamped between the two handle uprights.

Further, the clamping and fixing structure of the treatment head further comprises at least one limiting uprights opposite to the handle uprights, and the treatment head is stably clamped between the handle uprights and the limit uprights.

Further, the clamping and fixing structure of the treatment head further comprises an annular adapting base of the treatment head, the adapting base of the treatment head is detachably inserted at the edge of the vacancy position of the treatment head on the outer surface of the head sleeve base body; the handle uprights and the limit uprights are fixedly arranged on the outer surface of the adapting base of the treatment head.

Further, all the handle uprights are fixedly arranged on a first upright fixing plate, and the first upright fixing plate is fixedly connected with the adapting base of the treatment head in a radially adjustable position; the limiting uprights are fixedly arranged on a second upright fixing plate, the second column fixing plate is fixedly connected with the adapting base of the treatment head in a radially adjustable position; so that the treatment head is accurately and stably matched and arranged between the handle uprights and the limiting uprights.

Further, a base positioner is arranged at the front end of the head sleeve base body, and the base positioner is arranged with a positioning indicating end, which is just matched with the eyebrow center of the patient when the patient correctly wears the positioning adapter.

Further, a body of the base positioner is in the shape of a rhombic, and the downward acute angle end thereof is the positioning indicating end.

Further, the head sleeve base body is in a customized form, which is adapted to fit shape of the head of patient.

The method for making and using the precise treatment positioning adapter for a transcranial magnetic stimulator are as follows:

1). Production Method:
  1. Obtaining a suitable head sleeve base body.
  2. Arranging a vacancy position of the treatment head on a predetermined position of the head sleeve base body.
  3. Arranging the positioning and fixing structure of the treatment head on the head sleeve base body.

2). Use Method
  1. Wearing the precise treatment positioning adapter for a transcranial magnetic stimulator accurately for patients.
  2. Inserting the treatment head of the traditional transcranial magnetic stimulator properly on the positioning and fixing structure of the treatment head, and the treatment surface of the treatment head fits the patient's head.
  3. Turning on the transcranial magnetic stimulator to perform precise treatment on the patient's therapeutic target.

Further, the predetermined position of the head sleeve base body may be calculated and determined according to the image data of the patient's personal CT or MRI.

Using the positioning adapter of the present disclosure, it can quickly, accurately and effectively solve the problem of accurate positioning and setting of the treatment head of the transcranial magnetic stimulator, so that the transcranial magnetic stimulation can more accurately act on the treatment target of the patient, without the experience and professional quality of the operator, it makes the placement of the treatment head simple, convenient, accurate and effective, thereby greatly reducing the operation time of doctors and improving the curative effect, so that more patients can benefit from it.

BRIEF DESCRIPTION OF THE DRAWINGS

In order to make the above-mentioned purposes, features and advantages of the present disclosure more obvious and understandable, the specific embodiments of the present disclosure are described in detail below in combination with the accompanying drawings, in which.

Figure 1:
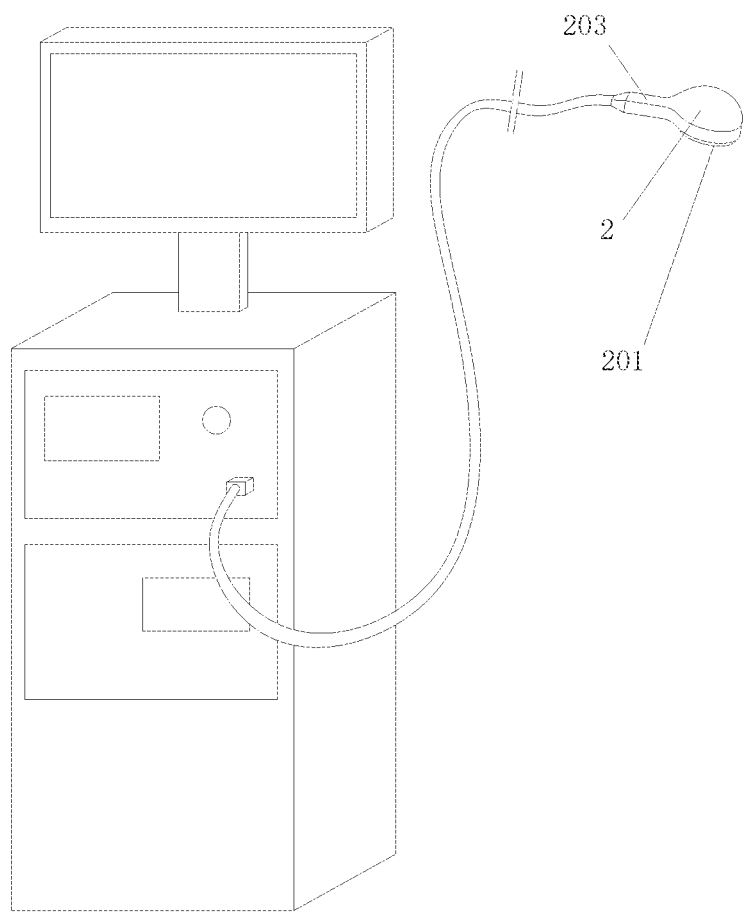
FIG. 1 is a schematic diagram of a transcranial magnetic stimulator.

In The Picture:
  a head sleeve base body 101. a vacancy position of the treatment head
  102. a base positioner 103. a pin hole upright 2. a treatment head
  201. a treatment surface 202. a handle 3. a head 4. handle uprights
  5. limiting uprights 6. adapting base of the treatment head
  7. a first upright fixing plate 8. a second upright fixing plate

DETAILED DESCRIPTION OF THE INVENTION

Below in conjunction with accompanying drawing and embodiment, the present invention is described in further detail:

FIG. 1 is a transcranial magnetic stimulator commonly used in major medical institutions, which has a treatment head 2 connected with a main body and a cable.

Figure 2:
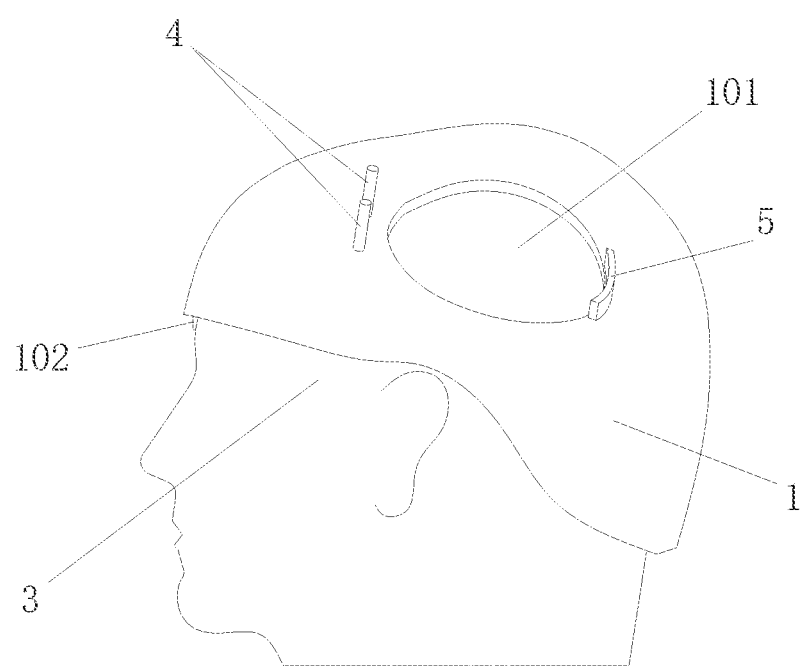
FIG. 2 is a schematic structural diagram of a precise treatment positioning adapter for a transcranial magnetic stimulator of the present disclosure.
Figure 3:
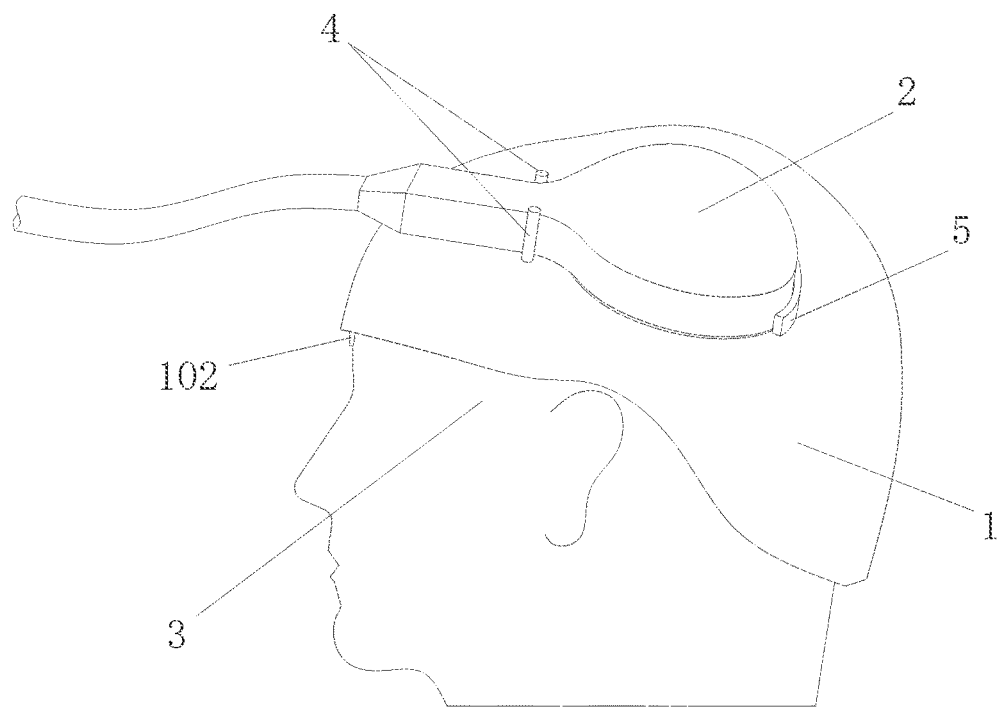
FIG. 3 is a schematic structural diagram of the treatment head matched and arranged on the positioning adapter.

FIG. 2 shows a precise treatment positioning adapter for a transcranial magnetic stimulator. When the patient needs treatment, only after accurately wearing the positioning adapter, the treatment head 2 of the magnetic stimulator can be easily, quickly, stably and accurately positioned to a predetermined position on the patient's head, thereby greatly reducing the doctor's operation time and improving the efficacy. The positioning adapter includes a head sleeve base body 1 and at least one positioning and fixing structure for the treatment head (if the patient only needs to perform treatment at one position, only one positioning and fixing structure for the treatment head can be provided; when the patient needs to perform treatment at two or more positions If there is no conflict in setting the treatment head positioning and fixing structures at these positions, a plurality of treatment head positioning and fixing structures can be set), and the positioning and fixing structure of the treatment head is as follows: a clamping and fixing structure of the treatment head is arranged at the edge of the vacancy position 101 of the treatment head on the outer surface of the head sleeve base body 1, so that the treatment head 2 is stably clamped, and the treatment surface 201 of the treatment head 2 pass through the vacancy position 101 of the treatment head and then fit to the head 3 of the patient, as shown in FIG. 3. The center of the vacant position 101 of the treatment head is the center of the treatment surface 201 after the treatment head 2 is matched and arranged, that is, the pointing position of the treatment target.

Since the shape of the head sleeve base body 1 can be various, as long as it can be stably fixed to the patient's head 3 and stably arranged on the clamping and fixing structure of the treatment head. When the head sleeve base body 1 is a hemispherical headgear, the vacancy position 101 of the treatment head is in the shape of a circular hole or other shapes matching the treatment head. When the head sleeve base body 1 is a frame structure, the vacancy position 101 of the treatment head can then be an open vacancy.

As shown in FIG. 1 and FIG. 2, the clamping and fixing structure of the treatment head may comprises at least two handle uprights 4, and the handle 202 of the treatment head 2 is matched and clamped between the two handle uprights 4. Of course, several handle uprights 4 can also be provided to facilitate the clamping of some handles 202.

When the treatment head 2 is matched and clamped between the handle uprights 4 through the handle 202, and is not stable enough, the clamping and fixing structure of the treatment head further comprises at least one limiting uprights 5 opposite to the handle uprights 4 (it can be one or more), and the treatment head 2 is stably clamped between the handle uprights 4 and the limit uprights 5.

Figure 4:
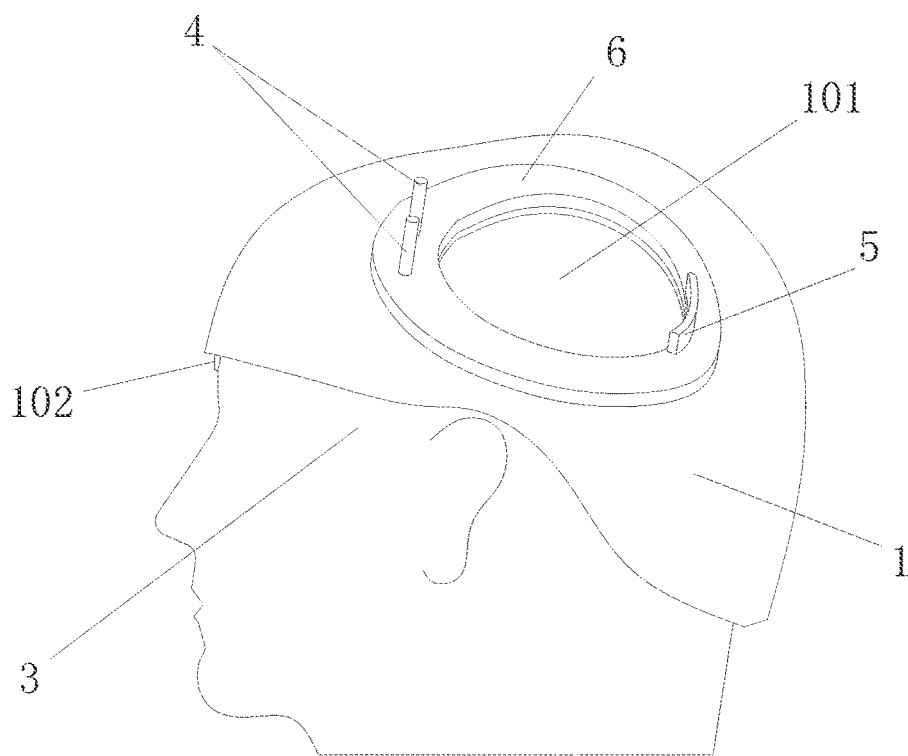
FIG. 4 is one of the structural schematic diagrams in which the positioning adapter is provided with the adapting base of the treatment head, and the state after the assembly is completed.
Figure 5:
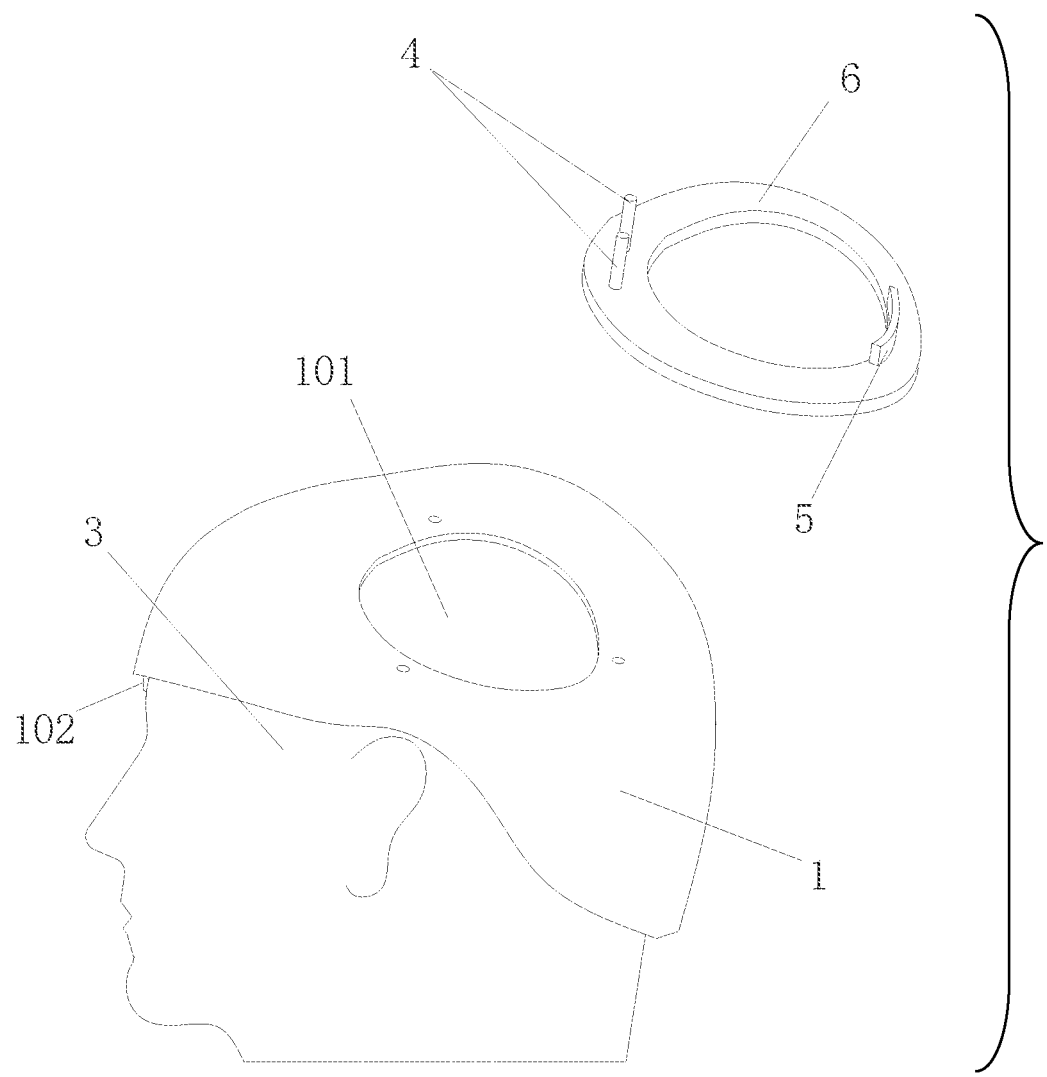
FIG. 5 is another structural schematic diagram in which the positioning adapter is provided with the adapting base of the treatment head, and the state that the treatment head adapter base is disassembled.

The above-mentioned handle uprights 4 and the limit uprights 5 can be directly fixed on the head sleeve base body 1, or can be detachably fixed and connected through a ring-shaped adapting base 6 of the treatment head, the adapting base 6 of the treatment head is detachably inserted at the edge of the vacancy position 101 of the treatment head on the outer surface of the head sleeve base body 1; the handle uprights 4 and the limiting uprights 5 are fixedly arranged on the outer surface of the adapting base 6 of the treatment head, as show in FIG. 4 and FIG. 5.

When the curvature of the head at the position where the vacancy position 101 of the treatment head is located is relatively small, the setting of the adapting base 6 of the treatment head may cause that the treatment surface 201 of the treatment head 2 cannot fit the patient's head because the thickness of the overlapping of the head sleeve base body 1 and the adapting base 6 of the treatment head is too thick. At this time, the head sleeve base body 1 needs to dig a groove on the outer surface, and insert the adapting base 6 of the treatment head into the groove to reduce the thickness of the assembled components here, so that after the treatment head 2 is installed, its treatment surface 201 can fit the patient's scalp.

Figure 6:
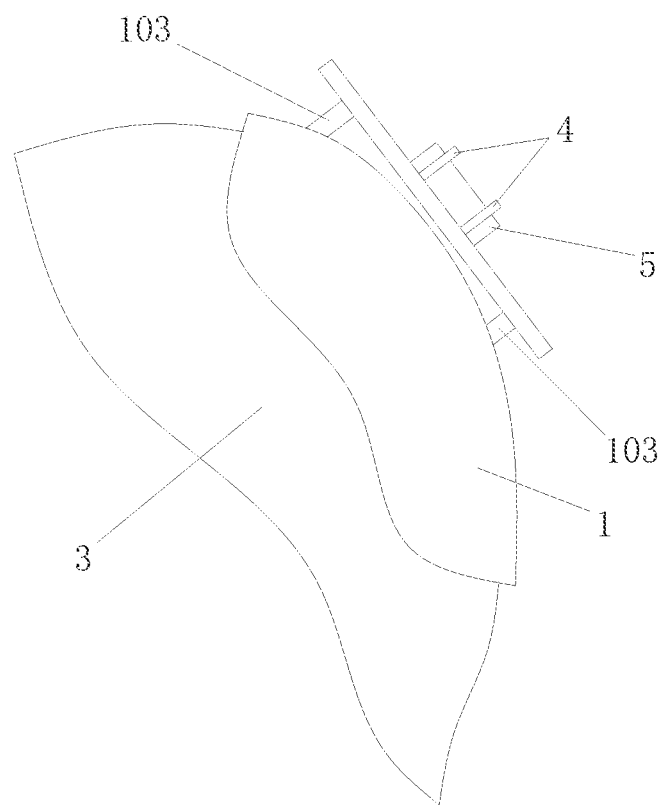
FIG. 6 is a schematic structural diagram of a pin hole upright is arranged on the head sleeve base body due to the excessive curvature of the curved surface to match positioning pin assembly of the adapting base of the treatment head, when the adapting base of the treatment head is provided.

In order to set the treatment head 2 on the adapting base 6 of the treatment head more smoothly, the outer surface of the adapting base 6 of the treatment head is generally set as a plane, and the curved surface curvature of the patient's head 3 at the predetermined treatment position where the vacancy position 101 of the treatment head is located may be relatively large. In this case, the following structural scheme can be adopted: the inner surface of the adapting base 6 of the treatment head adopts a curved surface shape that matches the curvature of the head, or the head sleeve base body 1 is provided with a raised platform there to adapt to the matching the plate-shaped annular treatment head to the adapting base 6 of the treatment head, or the head sleeve base body 1 is provided with a number of pin hole uprights 103 there to match the annular flat treatment head to the positioning pins at the bottom of the adapting base 6 of the treatment head (as shown in FIG. 6).

Figure 7:
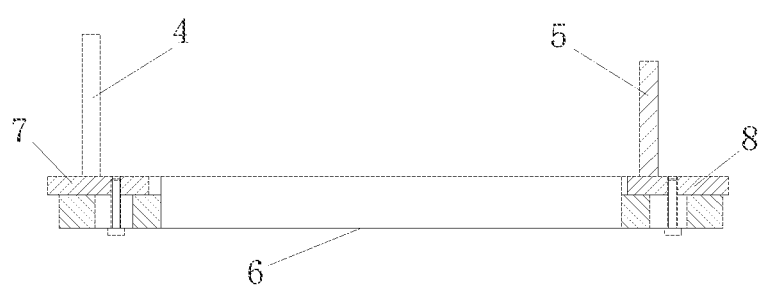
FIG. 7 is a schematic diagram of the radially adjustable structure of the handle uprights and the limiting uprights.

As shown in FIG. 7, since the shape and size of the treatment head 2 of the device applicable to patients may be different, in order that a set of adapters can be used for multiple treatment heads 2, the handle uprights 4 and the limiting uprights 5 can adopt a radial adjustable structure: all the handle uprights 4 are fixedly arranged on a first upright fixing plate 7, and the first upright fixing plate 7 is fixedly connected with the adapting base 6 of the treatment head in a radially adjustable position; the limiting uprights 5 are fixedly arranged on a second upright fixing plate 8, the second upright fixing plate 8 is fixedly connected with the adapting base 6 of the treatment head in a radially adjustable position; so that the treatment head 2 is accurately and stably matched and arranged between the handle uprights 4 and the limiting uprights 5. During installation, the first upright fixing plate 7 and the second upright fixing plate 8 can be adjusted and fixed when the treatment head 2 is in the standard treatment position (that is, the center of the treatment surface 201 of the treatment head 2 just coincides with the center of the vacancy position 101 of the treatment head), in this way, the positioning adapter can accurately and stably fit the treatment head 2. When the patient needs to fit another treatment head 2 with a different shape and size, the above treatment head 2 needs to simulate the operation of aligning, adjusting and fixing the first upright plate 7 and the second upright plate 8 again.

The first upright fixing plate 7, the second upright fixing plate 8 and the adapting base 6 of the treatment head can be fixedly connected in a radial adjustable position in a variety of conventional forms. FIG. 7 shows a structural form: the first upright fixing plate 7 and the second upright fixing plate 8 are pressed on the adapting base 6 of the treatment head, and the first upright fixing plate 7 and the second upright fixing plate 8 are provided with internal thread fixing holes, the adapting base 6 of the treatment head is provided with a waist hole extending radially along the adapting base 6 of the treatment head at a position corresponding to the internal thread fixing hole. The fixing screw passes through the waist hole and is fixedly connected with the internal thread fixing hole. At the same time, the position of the first upright fixing plate 7 and the second upright fixing plate 8 can be adjusted along the radial direction.

Further, In order that the patient can accurately wear the head sleeve base body 1 each time the positioning adapter is used, so that the position of the vacancy position 101 of the treatment head is accurately positioned at the "predetermined treatment position", a base positioner 102 is arranged at the front end of the head sleeve base body 1, and the base positioner 102 is arranged with a positioning indicating end, which is just matched with the eyebrow center of the patient when the patient correctly wears the positioning adapter. In this way, the patient can quickly and effectively adjust the precise position of the head sleeve base body 1 as long as they wear stably and make the positioning indicator end align with the eyebrow center of the patient during each use. A body of the base positioner 102 is in the shape of a rhombic, and the downward acute angle end thereof is the positioning indicating end. Of course, the base positioner 102 can also adopt other conventional structural forms, as long as it can play an auxiliary role in position correction when wearing the head sleeve base body 1.

The head sleeve base body 1 is in a customized form, which is adapted to fit shape of the head 3 of patient. Personal customization can be in the form of 3D modeling of the head sleeve base body 1 according to the scanning data of the patient's head 3, and then manufacturing a personalized head sleeve base body 1 that accurately fits the head 3 of a specific patient through 3D printing, or obtaining the personalized head sleeve base body 1 through other customization methods. Then, determining the treatment target according to the medical scanning data of the patient's head, so as to determine the predetermined treatment position for placing the treatment head 2, and set up the vacancy position 101 of the treatment head that matches the shape of the treatment head 2.

The above are only specific embodiments of the present disclosure, but the protection scope of the present disclosure is not limited thereto. Any person skilled in the art can easily think of changes or substitutions within the technical scope disclosed by the present disclosure should be included within the protection scope of the present disclosure. Therefore, the protection scope of the present disclosure should be based on the protection scope of the claims.

What is claimed is:

1. A precise treatment positioning adapter for a transcranial magnetic stimulator, comprising:
a head sleeve base body and at least one positioning and fixing structure of treatment head, the head sleeve base body is configured to be stably matched and worn on a head of a patient;
the at least one positioning and fixing structure of the treatment head consisting of: a vacancy position of the treatment head matching a shape of the treatment head is arranged at a predetermined treatment position of the head sleeve base body; a clamping and fixing structure of the treatment head is arranged at the edge of the vacancy position of the treatment head on the outer surface of the head sleeve base body, so that the treatment head is stably clamped, and the treatment surface of the treatment head pass through the vacancy position of the treatment head and then fit to the head of the patient;
the clamping and fixing structure of the treatment head comprises at least two handle uprights, and a handle of the treatment head is matched and clamped between the at least two handle uprights;
the clamping and fixing structure of the treatment head further comprises at least one limiting upright opposite to the at least two handle uprights, and the treatment head is stably clamped between the at least two handle uprights and the at least one limiting upright.

2. The positioning adapter according to claim 1, wherein the clamping and fixing structure of the treatment head further comprises an annular adapting base of the treatment head, the annular adapting base of the treatment head is detachably inserted at the edge of the vacancy position of the treatment head on the outer surface of the head sleeve base body; the at least two handle uprights and the at least one limiting upright are fixedly arranged on the outer surface of the annular adapting base of the treatment head.

3. The positioning adapter according to claim 2, wherein all the handle uprights are fixedly arranged on a first upright fixing plate, and the first upright fixing plate is fixedly connected with the annular adapting base of the treatment head in a radially adjustable position; the at least one limiting upright is fixedly arranged on a second upright fixing plate, the second upright fixing plate is fixedly connected with the annular adapting base of the treatment head in a radially adjustable position; so that the treatment head is accurately and stably matched and arranged between all the handle uprights and the at least one limiting upright.

4. The positioning adapter according to claim 3, wherein a base positioner is arranged at the front end of the head sleeve base body, and the base positioner is arranged with a positioning indicating end, which is just matched with the eyebrow center of the patient when the patient correctly wears the positioning adapter.

5. The positioning adapter according to claim 4, wherein the head sleeve base body is in a customized form, which is adapted to fit shape of the head of patient.

6. The positioning adapter according to claim 3, wherein the head sleeve base body is in a customized form, which is adapted to fit shape of the head of patient.

7. The positioning adapter according to claim 2, wherein a base positioner is arranged at the front end of the head sleeve base body, and the base positioner is arranged with a positioning indicating end, which is just matched with the eyebrow center of the patient when the patient correctly wears the positioning adapter.

8. The positioning adapter according to claim 7, wherein the head sleeve base body is in a customized form, which is adapted to fit shape of the head of patient.

9. The positioning adapter according to claim 2, wherein the head sleeve base body is in a customized form, which is adapted to fit shape of the head of patient.

10. The positioning adapter according to claim 1, wherein a base positioner is arranged at the front end of the head sleeve base body, and the base positioner is arranged with a positioning indicating end, which is just matched with the eyebrow center of the patient when the patient correctly wears the positioning adapter.

11. The positioning adapter according to claim 10, wherein the head sleeve base body is in a customized form, which is adapted to fit shape of the head of patient.

12. The positioning adapter according to claim 1, wherein the head sleeve base body is in a customized form, which is adapted to fit shape of the head of patient.

* * * * *